US007534221B2

(12) United States Patent
Pile-Spellman (10) Patent No.: US 7,534,221 B2
(45) Date of Patent: May 19, 2009

(54) DEVICES AND METHODS FOR PROTECTING AGAINST DISTAL EMBOLISMS

(75) Inventor: John Pile-Spellman, Pelham, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 594 days.

(21) Appl. No.: 10/852,044

(22) Filed: May 24, 2004

(65) Prior Publication Data

US 2005/0261726 A1 Nov. 24, 2005

(51) Int. Cl.
*A61M 37/00* (2006.01)
*A61M 1/00* (2006.01)

(52) U.S. Cl. .................... 604/5.01; 604/4.01; 604/6.02; 604/6.13; 422/44

(58) Field of Classification Search ................ 604/4.01, 604/6.08, 6.01–6.04, 6.09, 6.11, 6.13, 6.14, 604/6.16, 7, 19, 27, 28, 48, 500, 522, 506–510, 604/113, 114, 96.01, 907, 915; 422/44–48; 128/898; 600/466–469; 514/832, 833; 424/1.1, 424/1.2, 1.3, 2, 325, 372, 374, 377, 383, 424/283.1, 284.1, 93, 73, 93.1, 93.3, 93.7; 606/1, 2, 7, 8, 10, 13, 14, 27, 108, 191, 192, 606/194, 200

See application file for complete search history.

(56) References Cited

U.S. PATENT DOCUMENTS

| 4,535,284 A | 8/1985 | Groves et al. |
| 4,551,132 A | 11/1985 | Pásztor et al. |
| 4,750,493 A | 6/1988 | Brader |
| 4,752,586 A | 6/1988 | Ropars et al. |
| 4,920,963 A | 5/1990 | Brader |
| 4,987,154 A | 1/1991 | Long, Jr. |

(Continued)

FOREIGN PATENT DOCUMENTS

WO WO 98/24377 6/1998

(Continued)

OTHER PUBLICATIONS

Nidus Information Services, *What is a Stroke?*, Sep. 2001.

(Continued)

*Primary Examiner*—Leslie R Deak
*Assistant Examiner*—Philip Wiest
(74) *Attorney, Agent, or Firm*—Kenyon & Kenyon LLP (57) ABSTRACT

Endovascular intervention methods entail creating a temporary capillary block in the vasculature of at least a portion of a patient's organ, such as a hemisphere of the patient's brain, the capillary block essentially blocking blood flow through capillaries in the portion of the patient's organ, and performing the endovascular intervention. Distal embolism protection devices include a blood pump and at least one of a centrifuge element, a dialysis element, a cooling element, and a filtration element. The blood pump is generally capable of drawing blood from a patient's vein, circulating the blood through each of the elements so that a characteristic of a blood component may be manipulated therewith, and perfusing the modified blood into a patient's artery. A capillary block is thereby created in the vasculature of at least a portion of a patient's organ with manipulated blood components.

20 Claims, 3 Drawing Sheets

U.S. PATENT DOCUMENTS

| | | | |
|---|---|---|---|
| 5,383,854 | A | 1/1995 | Safar et al. |
| 5,432,089 | A | 7/1995 | Ryan et al. |
| 5,486,204 | A | 1/1996 | Clifton |
| 5,902,299 | A | 5/1999 | Jayaraman |
| 5,927,273 | A | 7/1999 | Federowicz et al. |
| 6,059,809 | A | 5/2000 | Amor et al. |
| 6,139,836 | A * | 10/2000 | Magnani et al. .......... 424/93.73 |
| 6,165,193 | A | 12/2000 | Greene, Jr. et al. |
| 6,258,115 | B1 * | 7/2001 | Dubrul ....................... 606/200 |
| 6,295,990 | B1 * | 10/2001 | Lewis et al. ................. 128/898 |
| 6,413,235 | B1 | 7/2002 | Parodi |
| 6,432,102 | B2 | 8/2002 | Joye et al. |
| 6,468,297 | B1 | 10/2002 | Williams et al. |
| 6,485,450 | B1 | 11/2002 | Owen |
| 2001/0031978 | A1 | 10/2001 | Kipke et al. |
| 2002/0045848 | A1 | 4/2002 | Jaafar et al. |
| 2002/0128638 | A1 | 9/2002 | Chauvet et al. |
| 2002/0138121 | A1 | 9/2002 | Fox |

FOREIGN PATENT DOCUMENTS

| | | |
|---|---|---|
| WO | WO 99/47191 | 9/1999 |
| WO | WO 02/05736 | 1/2002 |

OTHER PUBLICATIONS

Bachet, et al., *Brain Protection During Surgery of the Aortic Arch.*, http://www.ncbi.nlm.nih.gov/entrez/query.fcgi?cmd=Retrieve&db=PubMed&list_uids=1 (visited Nov. 2002).

Connolly, Jr., *Cerebral Protection in Homozygous Null ICAM-1 Mice After Middle Cerebral Artery Occlusion*, The American Society for Clinical Investigation, Inc., vol. 97, No. 1, Jan. 1996, pp. 209-216.

Ohki, et al., *Various Cerebral Protection Devices to Prevent Embolic Events During Carotid Stenting: An Overview*, http://www.vascularweb.org/doc/94 (visited Nov. 2002).

Ahmad et al., *Erythrocyte Membrane Stabilization by Indomethacin*, Indian Journal of Pharmacology, vol. 25, 1993, p. 173.

Oscar A. Mendiz, *Carotid Angioplasty: Techniques with and Without Cerebral Protection*, http://www.fac.org.ar/cvirtual/cvirteng/cienteng/pteng.ptc3291i/imendiz.htm, visited Nov. 2002.

Vitvitsky, et al., *Effect of Membrane Permeability to Anions on the Swelling Rate of Erythrocytes Treated With Amphotericin b or gramicidin d*, National Research Center for Hematology, pp. 255-260, www.sun.ac.za/biochem/btk/book/Vitvitsky.pdf, visited Nov. 2002.

David R. Caprette, *Organization of the Erythrocyte Membrane*, http://www.ruf.rice.edu/~bioslabs/studies/sds-page/rbcmembrane.html, May 17, 1996.

* cited by examiner

DEVICES AND METHODS FOR PROTECTING AGAINST DISTAL EMBOLISMS

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

The present invention relates to devices and methods for facilitating endovascular interventions, such as endovascular embolization of arteriovenous malformations ("AVMs"), arteriovenous fistulas ("AVFs"), angioplasty, and stenting, tumor embolization, and increased delivery of a therapeutic agent to targeted tissue.

Normal arterial and venous blood vessels connect to each other at the capillary level where blood flows at a relatively low rate and at a low pressure, which allows for the efficient transfer of nutrients, oxygen, and metabolic waste products between the blood and the body tissue. AVMs and AVFs, in contrast, are abnormal connections between arteries and veins at a level above the capillary level that occur in organs such as the brain. The abnormal connections provide a path of low resistance, which results in blood flow bypassing blood vessels at a vascular level lower than that where the abnormal connection occurs. The abnormal bypass may result in an ischaemic or hypoxic condition at least with respect to the tissue affected by the bypass. Moreover, the low resistance path provided by the malformation or fistula results in a relatively high blood flow rate through the malformation or fistula and at high pressure, which creates a risk of rupture that may result in a stroke or bleeding.

A variety of methods of treating AVMs and AVFs have been adopted. One approach has been to create an endovascular occlusion or embolization in the malformation or fistula by introducing a blocking material, such as a glue or polymer, typically in a liquid form via a catheter into the malformation or fistula. The liquid blocking material is typically introduced upstream of the AVM or AVF such that blood flow carries the blocking material downstream to the target site where the material sets to form the occlusion. This method of treating AVMS and AVFs, however, is prone to complications associated with the relative difficulty in performing the procedure. Introducing the blocking material upstream of the target, for instance, may result in the blocking material being carried away beyond or bypassing the abnormal connection to normal vasculature where the material will set to form unwanted embolisms that may result in a stroke with potentially catastrophic effects.

Arteriosclerosis (or, more properly, atherosclerosis) is the progressive narrowing and hardening of the arteries over time resulting from aging as well as other risk factors known to accelerate the process, such as high cholesterol, high blood pressure, smoking, diabetes, etc. Angioplasty, a common non-invasive method of treating such a stenosis, entails introducing a balloon-tipped catheter into the diseased blood vessel where the balloon is inflated to expand the blood vessel with the stenosis in order to improve blood flow through the vessel. Stenting has also been adopted as a method of treating a stenosis, either alone or in combination with angioplasty, particularly with respect to coronary and carotid arteries. Stenting entails introducing a stent, e.g., a device developed to keep the lumen of a blood vessel open, to maintain the patency of blood vessels. Endovascular procedures, such as angioplasty and stenting, however, typically cause embolic particles or plaque to dislodge from the site of the stenosis and pose a risk of distal embolisms. This is particularly problematic with arteries providing blood to the brain, such as the carotid artery.

Although chemotherapy treatments are designed to attack specific disease producing microorganisms or selectively destroy cancerous tissue, in practice the chemical treatment often has deleterious effects on normal tissue. Accordingly, in many instances the particular dosage for the chemotherapy treatment is a balance between the desire to eliminate the microorganism or cancerous tissue while limiting the damage to normal tissue. In this respect, the effectiveness of chemotherapy against the offending organism or tissue is limited by the potential harm to distal normal tissue.

Three noteworthy techniques and corresponding devices have been adopted in connection with carotid artery angioplasty and stenting to protect against distal embolisms: distal occlusion, distal filtration, and proximal occlusion. Although these techniques have proven to be necessary accompaniments, particularly with carotid artery angioplasty and stenting, the techniques have associated therewith a number of disadvantages, which are discussed below.

The distal occlusion technique entails expanding a balloon catheter downstream from the stenosis, which serves to block blood flow, which typically includes embolic particles dislodged during the angioplasty or stenting procedure, to the brain. The site of the angioplasty or stenting procedure is aspirated upon completion of the procures to remove the embolic particles from the site and the balloon catheter subsequently released so that normal blood flow through the carotid artery may be resumed. Distal occlusion, however, has a number of shortcomings. For instance, distal occlusion may not protect against embolic particles entering the blood stream and traveling to the brain via a patent carotid artery. Additionally, the procedure is relatively cumbersome, requiring the user to manipulate a number of endovascular tools, e.g., the blocking catheter, angioplasty catheter, aspiration catheter, etc., within the stenotic blood vessel. This problem is compounded particularly where the stenosis occurs in tortuous blood vessels or though which tortuous blood vessels the catheters must navigate to reach the stenosis.

The distal filtration technique entails placing a filtering medium via a catheter downstream from the stenosis in order to capture embolic particles that may be dislodged during the angioplasty or stenting procedures. Distal filtration, however, is similarly cumbersome and the filter medium is not capable of capturing particles smaller than the pore size of the filter medium. The filter medium may, in addition, thrombose, which may result in blood clots entering the blood stream, such as through a patent artery, posing a risk of a distal embolism.

Finally, proximal occlusion entails placing a blocking device upstream from the stenosis via a catheter to also block blood flow in the brain. Embolic particles dislodged during the angioplasty or stenting procedure are aspirated from the site, upon completion of the procedures, by temporarily reversing blood flow through the stenotic artery and draining the fluid from the site. Associated with proximal occlusion, however, is the potential for causing distinction or spasm in the artery.

Current methods for distal protection of normal tissue during embolization of a tumor include occlusion of the proximal vessel with a temporary or permanent agent. These methods are often unsatisfactory because collateral flow through the tumor often harms the normal tissue distal to the occlusion. Increasing the dose of a drug along with a partial embolization results in a breakdown of the blood brain barrier; however, these methods are difficult to control and may adversely affect non-target tissue.

There is therefore an ongoing need for methods and devices for facilitating endovascular interventions, such as the endovascular embolization, angioplasty, stenting, tumor embolization, etc., that reduce the risk of unwanted or distal embolisms. There is also a need for methods and devices for increasing the efficiency of targeted delivery of therapeutic agents to tissue.

SUMMARY OF THE INVENTION

The present invention provides devices and methods for protecting against distal embolisms that overcome at least some of the shortcomings in the art. In one aspect of the present invention, this is accomplished with an endovascular intervention method that includes the steps of creating a temporary capillary block in the vasculature of at least a portion of a patient's organ downstream from a site for an endovascular intervention sufficient to substantially or completely block blood flow through the capillaries in the particular portion of the patient's organ and performing the endovascular intervention. The term "temporary" is used herein to refer to a sufficient period of time to protect against distal embolisms while limiting the effects of hypoxia on the organ. Accordingly, temporary will vary depending on the resistance of the particular organ to hypoxia and the conditions under which protection is being provided. A temporary capillary block in the brain, for instance, may be created from about 1 to about 3 minutes, whereas a capillary block in another organ may be created for a longer period of time. The temporary capillary block generally prevents ischemic particles, which may be released during an endovascular intervention, from being carried away from the site of the intervention toward the blocked organ. A variety of endovascular interventions may be facilitated with the temporary capillary block, including endovascular embolization, angioplasty, and stenting. The capillary block may be created in a variety of organs, including the patient's brain, to protect against, for example, distal embolisms.

In one embodiment of this invention, the temporary capillary block is created with components of blood suspended therein, such as erythrocytes, by manipulating at least one characteristic of a blood component or of the blood that affects the ability of blood to circulate through the organ's or brain's vasculature. The relevant characteristics include, the size of the suspended component, the hematocrit of blood, the cell membrane deformability of suspended components, etc. The size of at least one suspended component, such as erythrocytes, may be increased to create the capillary block therewith. The size of erythrocytes, for instance, may be increased to about 12 μm thereby blocking capillaries in the relevant portion of a patient's organ, such as the brain. The increase in size may be accomplished by exposing the suspended components to a hypotonic fluid. With regard to the hematocrit of blood, it may be increased to about 60% thereby increasing the relative amount of erythrocytes in the blood to create the temporary capillary block therewith. Changes in cell membrane deformability can be obtained by, e.g., decreasing the temperature of the suspended component, discussed below, to affect the circulatory ability of suspended components. By stiffening the cell membranes, particularly erythrocytes cell membranes, the ability of the suspended components to circulate through the vasculature of a patient's organ, such as the brain, becomes limited such that a temporary capillary block may be created therein with the stabilized suspended components.

In one embodiment, the temporary capillary block is created by drawing blood from the patient, manipulating at least one characteristic of a suspended component in the drawn blood that affects the ability of blood to circulate through the organ's vasculature, and perfusing the blood having the manipulated suspended component into the patient at an artery. Blood is generally perfused upstream from the portion of the patient's organ targeted for the capillary block so that the capillary block may be created with the manipulated suspended component.

In another aspect of the present invention, an endovascular intervention method is provided that includes the steps of creating a temporary capillary block in the vasculature of a hemisphere of a patient's brain with erythrocytes having modified characteristics and performing the endovascular intervention. Erythrocyte characteristics may be modified by increasing erythrocyte size or stabilizing erythrocyte cell membranes, e.g., decreasing erythrocyte cell membrane permeability or increasing cell membranes stiffness.

In another aspect of the present invention, an endovascular intervention method is provided that includes the steps of drawing blood from a patient, manipulating at least one characteristic of erythrocytes suspended in the drawn blood that affects the ability of blood to circulate through the vasculature of a patient's brain, and perfusing the blood having the manipulated suspended component into the patient at a carotid artery. Blood is perfused upstream of a hemisphere of the patient's brain targeted for the capillary block such that a capillary block may be created with the manipulated erythrocytes.

In another aspect of the present invention, a distal embolism protection device is provided that includes a blood pump and at least one element or equivalent means for creating a temporary capillary block by manipulating at least one characteristic of a blood component that affects the ability of blood to circulate through a patient's vasculature connected to the pump. In one embodiment, the element selected from the group of elements consisting of: a centrifuge element, a dialysis element, a cooling element, and a filtration element. The blood pump is generally capable of drawing blood from a patient's vein, circulating the blood through each of the elements therewith manipulating at least one characteristic of a blood component that affects an ability of blood to circulate through a patient's vasculature, and perfusing the modified blood into a patient's artery. The capillary block is therefore created in the vasculature of at least a portion of a patient's organ, such as the brain, with the manipulated blood components.

In one embodiment, the device includes a dialysis element adapted to increase the size of erythrocytes suspended in blood drawn from the patient so that the capillary block may be created with erythrocytes increased size. In another embodiment, the device includes a dialysis element adapted to stiffen cell membranes of erythrocytes suspended in blood drawn from the patient so that the capillary block may be created with the erythrocytes with the stiffened cell membranes. The device may include a cooling element capable of cooling drawn blood to about 20 degrees C. thereby stiffening the cell membranes of erythrocytes suspended in the patient's blood so that the capillary block may be created with the erythrocytes with the stiffened cell membranes. The device may also include a centrifuge element adapted to increase hematocrit of blood drawn from a patient to about 60% so that the capillary block may be created with erythrocytes.

In another aspect of the present invention, an endovascular intervention assist device is provided that includes a blood pump and at least one element connected to the pump, the element selected from the group of elements consisting of: a centrifuge element, a dialysis element, a cooling element, and a filtration element. The blood pump is capable of drawing blood from a patient's vein, circulating the blood through each of the elements therewith manipulating at least one characteristic of erythrocytes that affects an ability of blood to circulate through a patient's brain, and perfusing the modified blood into a patient's carotid artery. A capillary block may be created in vasculature of a hemisphere of the patient's brain with the manipulated blood erythrocytes.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF PREFERRED EMBODIMENTS

Although the methods and devices may be described herein by way of example in relation to specific endovascular interventions or particular patient anatomy, it is understood that the methods and devices of the present invention, are equally applicable to interventions or anatomy not disclosed herein that may benefit from the methods and devices of the present invention, and are therefore not limited thereto.

Figure 1:
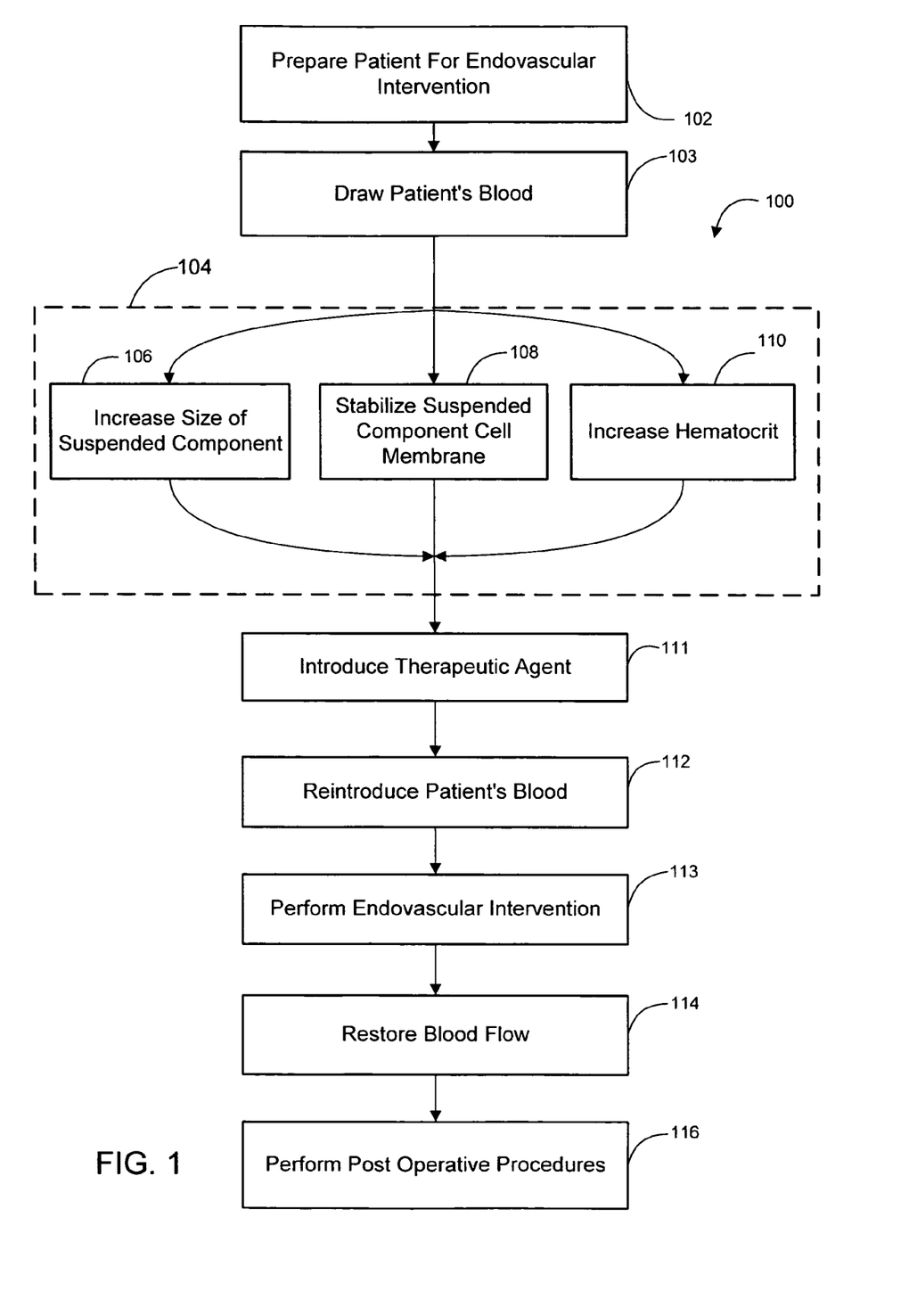
FIG. 1 is a flow chart of a method of facilitating endovascular interventions according to one embodiment of the present invention.

Referring to FIG. 1, a method of facilitating endovascular interventions 100 according to one embodiment of the present invention begins at step 102 by preparing a patient for an endovascular intervention. A patient is used herein to denote a subject to which the methods and devices described herein may be applied, such as humans, animals, etc. An endovascular intervention denotes any medical or surgical procedure that involves intraluminal access of a patient's vasculature. Endovascular interventions therefore include procedures that are performed mostly intraluminally, such as endovascular embolization, angioplasty, stenting, etc., as well as those that entail at least some degree of intraluminal activity, such as targeted delivery of therapeutic agents and those involving intraluminal navigation to access a site targeted for the intervention. A therapeutic agent is used herein to denote any substance used for the treatment, prevention, or discovery of a disease, illness, or disorder, including any protein, polypeptide, peptide, nucleic acid (including DNA, RNA, and genes), antibody, Fab fragment, F(ab')2 fragment, molecule, compound, antibiotic, drug, and any combinations thereof. The step of preparing a patient for endovascular intervention may vary depending on the particular procedure for which the present invention is adopted as a means for facilitating or otherwise assisting therewith, and may include a plurality of steps. Preparing a patient, for instance, may include administering anesthesia, attaching diagnostic or therapeutic devices to the patient, establishing intraluminal access to the patient's vasculature, such as at the femoral artery, brachial artery, carotid artery, etc.

In one embodiment, the endovascular intervention is facilitated by creating a temporary capillary blocking in the vasculature of at least a portion of a patient's organ, step 104. In relation to endovascular embolization, the temporary capillary block is created in at least a portion of a patient's brain, such as a hemisphere of the brain, which results in essentially blocking or substantially reducing blood flow though normal vessels, e.g., vessels having a capillary level connection, in the relevant portion of the brain while not also doing so with respect to abnormal vasculature, such as AVMs and AVFs. The capillary block therefore limits blood flow to the AVM or AVF so that blocking material introduced upstream of the targeted AVM or AVF to create the embolization therein is less likely to migrate away from the abnormal vasculature towards normal vasculature. In relation to angioplasty and stenting, such as of the carotid artery, the temporary capillary block similarly essentially blocks or substantially reduces blood flow through normal vasculature of at least a portion of an organ, such as the brain, so that embolic particles released during the endovascular intervention are less likely to migrate toward the capillary blocked vasculature. It is understood that the time limit for which the temporary capillary block may be created varies depending on the resistance of the particular organ to the damaging effects of ischemia. The capillary block in the patient's brain, for instance, may be maintained for less than three minutes, whereas for other organs, such as the heart the block may be maintained for a longer duration.

Figure 2:
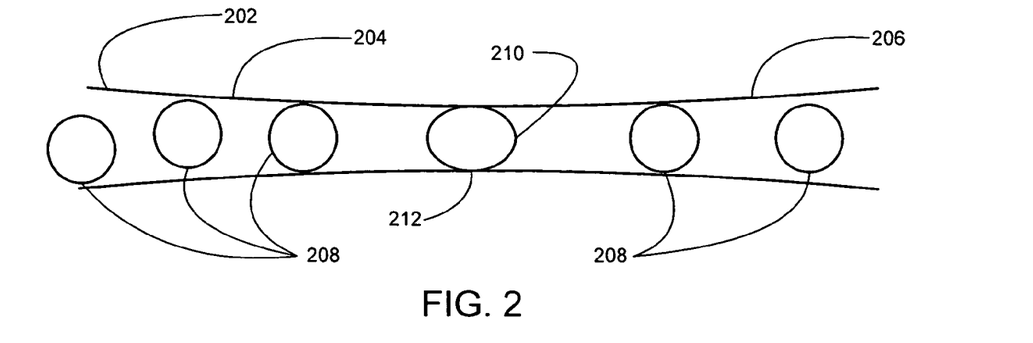
FIGS. 2-5 are cross section views of a patient's vascular anatomy illustrating capillary blocking techniques according to a number of embodiments of the present invention.

Blood is generally composed of four basic elements, including a liquid plasma and, suspended therein, erythrocytes (red blood cells), leucocytes (white blood cells), and platelets. As shown in FIG. 2, the ability of blood to circulate is largely dependent on the ability of the suspended components 208, such as the erythrocytes, to pass from the arterial side 204 of the capillaries 202 through the narrow capillary tissue 212 to the venous blood side 206 of the capillaries 202. The size of the suspended components 208, e.g., the cross sectional diameter, is often about or slightly larger than the size of the narrow capillary tissue 202. Thus, in order for the suspended components 208 to pass through the capillaries, the suspended components 208 must deform to a certain degree into a deformed suspended component 210 to match the size of the capillary through which the suspended component 208 must pass.

The present invention capitalizes on the rather constricted anatomical relationship between the suspended components 208 and the capillaries 202 to create a temporary capillary block. Thus, the capillary block in the vasculature of at least a portion of a patient's organ may be accomplished by manipulating characteristics of the capillaries 202 or the blood components 208 that may affect the ability of blood to circulate through the patient's vasculature so that at least one of the suspended components 208, such as the erythrocytes, are prevented from passing through the narrow capillary tissue 212 thereby creating the capillary block therewith. The term characteristic is used herein to generally denote definable properties, such as those relating to size, permeability, hematocrit, etc. Manipulating generally denotes changing or otherwise modifying a characteristic.

It is understood that the capillaries or the blood components characteristics may be manipulated in a variety of ways to achieve the capillary block. A capillary block, for instance, may be created by constricting the capillaries 202 temporarily so that at least one of the suspended components 208, such as the erythrocytes, is prevented from passing though the capillaries, which results in the suspended component 208 blocking and, consequently essentially blocking or substantially reducing blood flow between the arterial and venous sides 204, 206 of the capillaries 202. Alternatively, or in addition, the characteristics of suspended components 208 or of the blood may be manipulated to similarly essentially block or substantially reduce blood flow through the capillaries 202.

Figure 3:
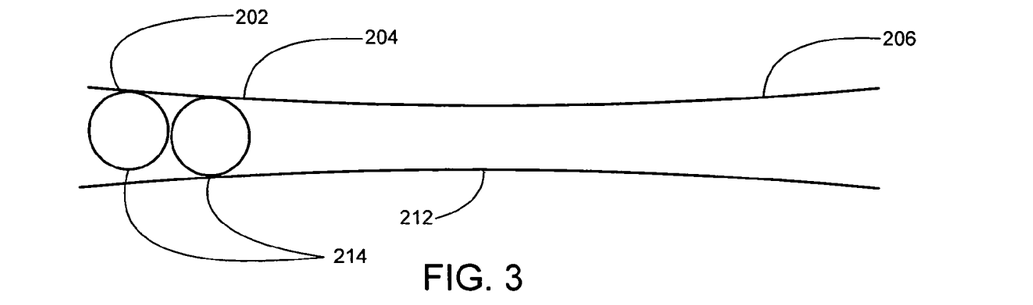

Referring back to FIG. 1, in one embodiment, the capillary block is created at step 106 by sufficiently increasing the size of at least one suspended component in the blood 208, such as the erythrocytes, or a portion thereof, so that the suspended component 208 present in the patient's blood is prevented from passing thought the narrow capillary tissue 212. A capillary block is thereby created with the suspended components having the increased size, which results in essentially blocking or substantially reducing blood flow through the capillaries 202 of the patient's organ, or a portion thereof. As shown in FIG. 3, the size of at least one suspended component 208 is increased sufficiently from a normal size to a swollen size, which results in a swollen suspended component 214 that is too large to pass though the narrow capillary tissue 212. The swollen suspended component 214 thus blocks the capillaries resulting in essentially blocking or substantial reducing blood flow through the capillaries 202. In one embodiment, the size, e.g., diameter, of erythrocytes present in the patient's blood are caused to swell from a normal size of about 7 μm to a swollen size of about 12 μm resulting in the capillary block therewith. In another embodiment, at least a portion of the erythrocytes in the blood are caused to swell from a normal size to a swollen size of about 10 μm.

Various methods and substances may be used alone or in combination to cause suspended components to increase in size or swell. In one embodiment, at least one of the suspended components 208, such as the erythrocytes, are caused to swell by exposing at least a portion thereof to a hypotonic fluid, such as hypotonic $H_2O$. A hypotonic fluid is generally one having a lesser osmotic pressure than a reference fluid, which in this case is the blood plasma. Exposing blood to the hypotonic fluid through a dialysis membrane, for instance, will result in water entering the erythrocytes by osmosis thereby causing the increase in size or swelling. The degree of the swelling may be controlled and hemolysis prevented by controlling the osmolarity of the hypotonic $H_2O$ or by exposing the suspended components to a hypertonic fluid. A hypertonic fluid is generally one that negates the effects of the exposure to the hypotonic fluid resulting in, e.g., osmotic shrinking.

Figure 4:
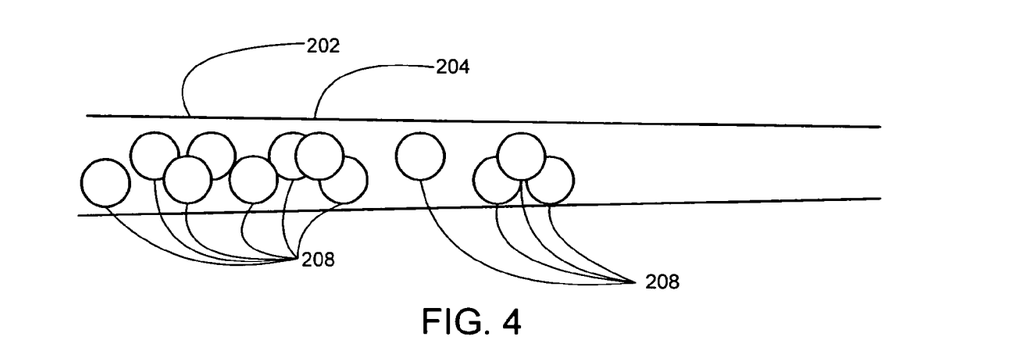

Referring back to FIG. 1, the temporary capillary block may also be accomplished at step 110 by increasing the hematocrit of at least a portion of the patient's blood. Hematocrit generally refers to the relative volume of blood occupied by erythrocytes. The average hematocrit is for human males about 40.7% to about 50.3% and for human females about 36.1% to about 44.3%. The increased hematocrit with a corresponding increase in the viscosity of the blood results in a decrease in the blood flow rate though the capillaries, as shown in FIG. 4. In one embodiment, the hematocrit of at least a portion of a patient's blood is increased to about 50% to 60%, which results in essentially blocking or substantially reducing blood flow through the capillaries 202.

Figure 5:
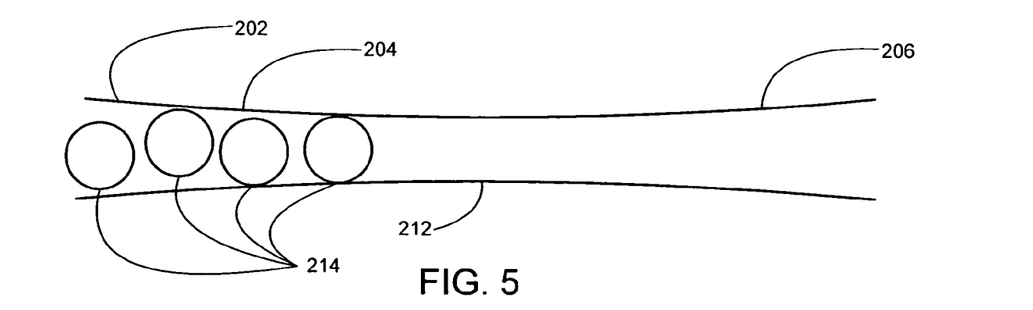

The temporary capillary block may also be accomplished at step 108 by stabilizing the cell membrane or the cell volume of at least one of the suspended components 208. As noted above, in order for some suspended components 208, such as erythrocytes, to pass through the narrow capillary tissue 212, the suspended components 208 must deform to about the size of the narrow capillary tissue 212. The deformation results in a corresponding change in the cellular volume or membrane of the suspended component 208, which is facilitated at least in part by the permeability or plasticity of the cell membrane, respectively. By stabilizing the cell membrane, e.g., by decreasing cell membrane permeability or by increasing cell membrane stiffness, changes to the suspended component 208 may be limited, which correspondingly limits the ability of the suspended component 208 to deform and thereby pass through narrow capillary tissue 212. The suspended components with the stabilized membrane 214 therefore create the capillary block which results in essentially blocking or substantial reducing blood flow through the capillaries 202, as shown in FIG. 5. It is understood that the method for stabilizing cell membranes may be accomplished in a variety of ways, such as by cooling the patient's blood or by exposing the patient's blood to substances that decrease cell membrane permeability or deformability. In one embodiment, cell membrane stiffness is increased by cooling at least a portion of the patient's blood containing the suspended components 208 from a normal temperature of about 38 degrees C. to about 20 degrees C. thereby resulting in increased cell stiffness of at least one suspended component 208, or a portion thereof.

Substances that may be used to manipulate characteristics of blood vessels, the suspended components 208, or the blood, as described above, may be administered intravenously or intramuscularly in preparation for the endovascular intervention. Alternatively, or in addition, characteristics of the suspended components 208 or blood may be manipulated by drawing at step 111 a portion of the patient's blood containing the suspended components 208, exposing or treating the blood to achieve the desired manipulation of a characteristic, such as an increase in the size of suspended components, decrease in cell membrane permeability or deformability, increase in hematocrit, etc., and reintroducing the exposed or treated blood into the patient's vasculature, such as in an artery upstream of the portion of the patient's organ targeted for the capillary block, by either infusing or perfusion at step 112. Blood may be drawn, for instance, from a vein and infused or perfused into an artery upstream of the patient's organ targeted for the capillary block, or a portion thereof, such as a hemisphere of the patient's brain.

Once the capillary block has been established, the endovascular intervention may then be performed at step 113. Imaging technology, such as angiography, or magnetic resonance imaging ("MRI"), may be used to determine whether or not the capillary block has been established. With regard to endovascular embolization a catheter is introduced into a patient's vascular anatomy, such as through the femoral, brachial, or carotid arteries, with or without the aid of imaging technology, and navigated toward the target abnormal vasculature where a blocking material may be introduced to create an embolization therein with the aid of the capillary block described herein. In relation to angioplasty and stenting, a balloon catheter is similarly introduced into the target blood vessel with the stenosis where the angioplasty balloon may be used to expand the area of the stenosis and a stent implanted to maintain patency also with the aid of the capillary block. The capillary block may be used either alone or in combination with other distal embolism protection devices, such as the distal occlusion, proximal occlusion, and distal filtering devices, to further facilitate endovascular interventions.

As noted above, with regard to tumor treatments, chemotherapeutic effects often are limited due to the possibility of toxicity to surrounding non-cancerous tissue. Temporary capillary blockage in accordance with the present invention of normal surrounding tissue during intra-arterial chemoembolization would mitigate the potential adverse effects to normal tissue while allowing higher concentrations of the therapeutic agent to be delivered to the tumor. Accordingly, the temporary capillary block may be used to increase exposure of the targeted tissue bed to a given therapeutic agent, which results in greater absorption of the therapeutic agent into the tissue thereby increasing the effectiveness of the therapy with regard to the targeted tissue. This aspect of the invention may generally be achieved by introducing at step 112 the therapeutic agent into the patient's blood with the manipulated components prior to perfusion, which will increase the agent's absorption fraction. Absorption of the drug or chemical is related to its extraction fraction according to the following algorithm:

$$EF \approx \int_{time} A-V \text{ difference} \times SP$$

where EF refers to the extraction fraction,
A–V difference refers to the arterio-venous difference, and
SP refers to surface permeability.

Blood flow may then be restored at step 114 after or at about the completion of the endovascular intervention. Blood flow may be restored by reversing any changes made to characteristics of the blood vessels, suspended components, or the blood to achieve the capillary block. The size increase in the suspended components 208, for instance, may be reversed by exposing the suspended components to a hypertonic fluid or by heating the patient's blood to a normal temperature. Changes to cell membrane permeability or stiffness may be reversed by exposing the suspended components to a substance to increase cell compliance and an increase in hematocrit may be reduced to normal levels by infusing the patient with plasma. Alternatively, reversal occurs without intervention such as with the expected normalization of the erythrocytes, for example, back to a normal size. Once blood flow is restored, postoperative procedures, including closing any surgical openings, reversing any effects of anesthesia, removing diagnostic or therapeutic devices attached to the patient, etc., may then be performed at step 116.

Figure 6:
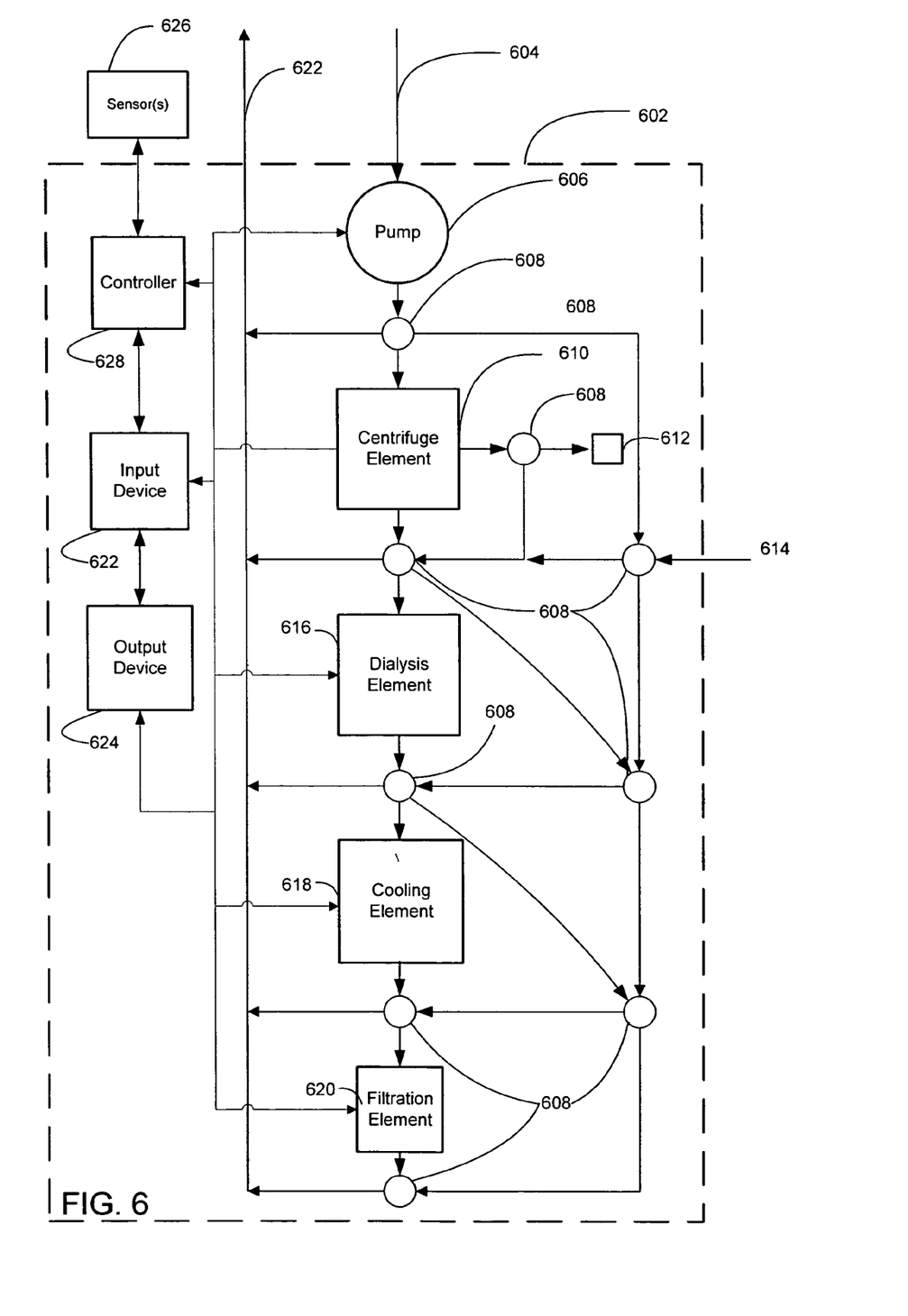
FIG. 6 is block diagram of a device useful in facilitating endovascular interventions according to one embodiment of the present invention.

Referring to FIG. 6, a device 600 that may be used to facilitation endovascular interventions according to the teachings of the present invention includes a blood pump 606 and blood manipulation elements 610, 616, 618 selectively used or in combination manipulate characteristics of the patient's blood or at least one of the suspended components therein. A blood pump is generally a mechanical pump capable of providing the necessary vacuum to draw blood from the patient and pressure to infuse or perfuse the blood with the manipulated characteristics into the patient while also avoiding hemolysis. In one embodiment, the vacuum side of the pump is connected to a venous cannula 604 which is cannulated to a patient's vein from which blood is drawn and the pressure side of the pump connected to at least one element that is used to manipulate characteristics of the blood or suspended components thereof.

The elements capable of manipulating characteristics of the patient's blood, and thereby providing a means for creating a temporary capollary block, include a centrifuge element 610, a dialysis element 616, a cooling element 618, and a filtration element. In one embodiment, the pump 606 and the particular elements are connected to each other with a plurality of flow control valves 608 that are generally used to control the amount and direction of blood or components thereof flowing through the device 602. The flow control valves 608, for instance, may be arranged such that all the blood drawn from the patient travels though each particular element of the device, or to a selected one or more of the available elements. For example, the blood drawn from the patient with the blood pump 606 may exit the pump, enter the cooling and filtration elements 618, 620 in series, and back into the patient via an arterial cannula 622.

Changes in hematocrit of the patient's blood may generally be accomplished with the centrifuge element 610, which is generally a device that separates the liquid component of the blood, i.e., the plasma, from the suspended components. Hematocrit increases are achieved by removing at least a portion of the separated plasma from the blood or adding suspended components thereto from an external source 614. The removed blood plasma may be stored in a storage tank 612 for later use, for example, to restore the hematocrit of the patient's blood to normal or preoperative levels. The external source 614 may also provide access for the introduction or mixing of a therapeutic agent with the patient's blood.

Changes to the size or diameter, stiffness, or permeability of the suspended components may be accomplished with the dialysis element 616 or the cooling element. The dialysis element 616 is generally a device having a plurality of chambers separated by a semi-permeable membrane, which allows an ionic exchange between fluids in the chambers that produces a change in the osmotic pressure of at least one of the fluids. Blood is placed in one of the chambers and either a hypotonic or a hypertonic solution placed in another that will result in the suspended components, such as the erythrocytes, to either swell or shrink, respectively. The cooling element 618 is generally a heat exchange apparatus that may be used to selectively cool or heat the blood pumped through the element in a manner to cause the suspended components to swell. The element may be, for example, a solid-state type cooler, a refrigeration cycle cooler, etc. Changes to cell membrane permeability may similarly be accomplished with a dialysis element.

The device 600 also includes a filtration element 620. The filtration element generally filters debris, such as blood clots, that may appear in the treated blood. An ABS or polystyrene filter medium may be used that generally has a pore size sufficient to allow the suspended components in the blood to pass. Readily available transfusion filters having a pore size from between 150 μm to 250 μm may be used for filtration.

The device 600 may also include at least one input device 622, which allows a user to selectively engage or vary the output of one or more of the elements of the device. The input device 622 may be a button, dial, switch, mouse, keyboard, touchpad, or a combination thereof. The device 600 may also include an output device 624 for communicating relevant information, such as an alarm or operating data, e.g., pressure, temperature, osmolarity, etc., to the user. The output device 624 may be one that provides an audible alarm, such as a speaker or buzzer, or one that provides a visual alarm or indication, such as a light or a display. In one embodiment, the device output device 624 provides a user interface for the user of the device 600 to monitor operating data and to adjust the operating variables accordingly.

The device 600 may further include a controller 628 or other control circuitry for operating, automatically or otherwise, one or more elements of the device 600. The controller generally provides a drive signal to operate various elements of the device 600, such as the pump 606, flow control valves 608, centrifuge element 610, dialysis element 616, cooling element 618, and filtration element 620. The operation of the individual elements, such as turning the elements on or off, or varying the speed or other function, may be driven based on user input, e.g., from the input device 622, programming for providing automated or semi-automated operation, or a combination thereof. The device may also include one or more sensors 626 or equivalent circuitry, external or internally, for monitoring operating conditions, including pressure, blood flow, speed, osmolarity, temperature, etc., and adjusting the conditions accordingly to provide the capillary block as described herein.

While the invention has been described and illustrated in connection with preferred embodiments, many variations and modifications as will be evident to those skilled in this art may be made without departing from the spirit and scope of the invention, and the invention is thus not to be limited to the precise details of methodology or construction set forth above as such variations and modification are intended to be included within the scope of the invention.

I claim:

1. An endovascular intervention method comprising:
    creating a temporary capillary block in vasculature of at least a portion of a patient's organ downstream from a site for an endovascular intervention, the capillary block essentially blocking blood flow through capillaries in the portion of the patient's organ; and
    performing the endovascular intervention;
    wherein creating the temporary capillary block comprises manipulating at least one characteristic of a blood component that affects an ability of blood to circulate though the organ's vasculature, the capillary block created by virtue of manipulated suspended component.

2. The method of claim 1, comprising performing an endovascular intervention selected from the group consisting of endovascular embolization, angioplasty, and stenting.

3. The method of claim 1, comprising creating a temporary block in the vasculature of a patient's brain.

4. An endovascular intervention method comprising:
    creating a temporary capillary block in vasculature of at least a portion of a patient's organ downstream from a site for an endovascular intervention, the capillary block essentially blocking blood flow through capillaries in the portion of the patient's organ; and
    performing the endovascular intervention;
    wherein creating the temporary capillary block comprises manipulating at least one characteristic of erythrocytes suspended in the patient's blood that affects the ability of blood to circulate through the organ's vasculature, the capillary block created with the manipulated erythrocytes.

5. An endovascular intervention method comprising: creating a temporary capillary block in vasculature of at least a portion of a patient's organ downstream from a site for an endovascular intervention, the capillary block essentially blocking blood flow through capillaries in the portion of the patient's organ;
    performing the endovascular intervention; and
    creating the temporary capillary block in the vasculature of at least a portion of a patient's brain by increasing hematocrit of the blood in the patient's organ.

6. The method of claim 5, comprising increasing the hematocrit of the patient's blood to about 60%.

7. An endovascular intervention method comprising:
    creating a temporary capillary block in vasculature of at least a portion of a patient's organ downstream from a site for an endovascular intervention, the capillary block essentially blocking blood flow through capillaries in the portion of the patient's organ; and
    performing the endovascular intervention;
    wherein creating the temporary capillary block in the vasculature of at least a portion of the patient's organ comprises increasing the size of at least one suspended component in the patient's blood, the capillary block created with the suspended component having the increased size.

8. An endovascular intervention method comprising:
    creating a temporary capillary block in vasculature of at least a portion of a patient's organ downstream from a site for an endovascular intervention, the capillary block essentially blocking blood flow through capillaries in the portion of the patient's organ; and
    performing the endovascular intervention;
    wherein creating the temporary capillary block in the vasculature of at least a portion of the patient's organ comprises increasing the size of erythrocytes suspended in a patient's blood, the capillary block created with the erythrocytes having the increased size.

9. The method of claim 8, comprising increasing the size of erythrocytes suspended in the patient's blood to about 12 µm.

10. The method of claim 8, wherein increasing the size of erythrocytes suspended in the patient's blood comprises exposing at least a portion of the patient's blood to a hypotonic fluid.

11. An endovascular intervention method comprising:
    creating a temporary capillary block in vasculature of at least a portion of a patient's organ downstream from a site for an endovascular intervention, the capillary block essentially blocking blood flow through capillaries in the portion of the patient's organ; and
    performing the endovascular intervention;
    wherein creating the temporary capillary block in the vasculature of at least a portion of the patient's organ comprises stabilizing a cell membrane of erythrocytes suspended in the patient's blood, the capillary block created with the stabilized-membrane erythrocytes.

12. The method of claim 11, wherein stabilizing a cell membrane of erythrocytes suspended in the patient's blood comprises at least one of decreasing cell membrane permeability and increasing cell membrane stiffness.

13. An endovascular intervention method comprising:
    creating a temporary capillary block in vasculature of at least a portion of a patient's organ downstream from a site for an endovascular intervention, the capillary block essentially blocking blood flow through capillaries in the portion of the patient's organ; and
    performing the endovascular intervention;
    wherein creating the temporary capillary block in the vasculature of the patient's organ comprises:
    drawing blood from the patient;
    manipulating at least one characteristic of a suspended component in the drawn blood that affects the ability of blood to circulate through the organ's vasculature; and
    perfusing the blood having the manipulated suspended component into the patient at an artery upstream from the portion of the patient's organ targeted for the capillary block, the capillary block created with the manipulated suspended component.

14. The method of claim 13 comprising introducing a therapeutic agent into the blood drawn from the patient.

15. An endovascular intervention method comprising:
    creating a temporary capillary block in vasculature of a hemisphere of a patient's brain with erythrocytes having modified characteristics, erythrocyte characteristics modified by at least one of increasing erythrocyte size and decreasing erythrocyte cell membrane permeability; and
    performing the endovascular intervention.

16. An endovascular intervention method comprising,
drawing blood from a patient;
  manipulating at least one characteristic of erythrocytes suspended in the drawn blood that affects the ability of blood to circulate through vasculature of a patient's brain; and
  perfusing the blood having the manipulated suspended component into the patient at a carotid artery upstream of a hemisphere of the patient's brain targeted for a temporary capillary block,
  creating the temporary capillary block with the manipulated erythrocytes.

17. A distal embolism protection device comprising a blood pump and at least one element connected to the pump, the element selected from the group of elements consisting of:
  a centrifuge element;
  a dialysis element;
  a cooling element; and
  a filtration element, the blood pump capable of drawing blood from a patient's vein, circulating the blood through each of the elements therewith manipulating at least one characteristic of a blood component that affects an ability of blood to circulate through a patient's vasculature, and perfusing the modified blood into a patient's artery, a capillary block created in vasculature of at least a portion of a patient's organ with the manipulated blood components; and
  a dialysis element configured to stabilize a size of erythrocytes suspended in blood drawn from the patient, the capillary block created with erythrocytes increased in size.

18. The device of claim 17, comprising a cooling element capable of cooling drawn blood to about 20 degrees C. thereby increasing cell membrane stiffness of erythrocytes suspended in the patient's blood, the capillary block created with the erythrocytes with the stiffened cell membranes.

19. The device of claim 17, comprising a centrifuge element adapted to increase hematocrit of blood drawn from a patient to about 60%, the capillary block may be created with erythrocytes.

20. A distal embolism protection device comprising a blood pump and at least one element connected to the pump, the element selected from the group of elements consisting of:
  a centrifuge element;
  a dialysis element;
  a cooling element; and
  a filtration element, the blood pump capable of drawing blood from a patient's vein, circulating the blood through each of the elements therewith manipulating at least one characteristic of a blood component that affects an ability of blood to circulate through a patient's vasculature, and perfusing the modified blood into a patient's artery, a capillary block created in vasculature of at least a portion of a patient's organ with the manipulated blood components; and a dialysis element configured to stabilize erythrocytes suspended in blood drawn from the patient, the capillary block created with stabilized erythrocytes.

* * * * *